United States Patent [19]
Diehl et al.

[11] Patent Number: 5,399,627
[45] Date of Patent: Mar. 21, 1995

[54] RADIAL STYRENE-ISOPRENE-BUTADIENE MULTI-ARMED BLOCK COPOLYMERS AND COMPOSITIONS AND ARTICLES CONTAINING BLOCK COPOLYMERS

[75] Inventors: Charles F. Diehl; Jean M. Tancrede; Gary R. Marchand, all of Baton Rouge, La.

[73] Assignees: The Dow Chemical Company, Midland, Mich.; Exxon Chemical Patents, Inc., Linden, N.J.

[21] Appl. No.: 158,200

[22] Filed: Nov. 24, 1993

Related U.S. Application Data

[63] Continuation-in-part of Ser. No. 705,193, May 24, 1991, Pat. No. 5,292,819, which is a continuation-in-part of Ser. No. 393,545, Aug. 11, 1989, Pat. No. 5,143,968.

[51] Int. Cl.[6] .................... C08F 297/04; C08L 53/00
[52] U.S. Cl. .................................. 525/314; 525/88; 525/95; 525/98; 428/260; 428/261; 428/264; 428/265; 428/500; 428/507; 428/511
[58] Field of Search ............. 525/314, 88, 95, 98; 428/260, 261, 264, 265, 507, 511, 500

[56] References Cited

U.S. PATENT DOCUMENTS

| | | | |
|---|---|---|---|
| 3,149,182 | 9/1964 | Porter | 260/879 |
| 3,281,383 | 10/1966 | Zelinski et al. | 260/23.7 |
| 3,658,740 | 4/1972 | Marrs et al. | 260/27 |
| 3,753,936 | 4/1973 | Marrs | 260/27 R |
| 3,985,830 | 10/1976 | Fetters et al. | 260/880 B |
| 4,133,731 | 1/1979 | Hansen et al. | 204/159.17 |
| 4,136,137 | 1/1979 | Hsieh et al. | 206/880 B |
| 4,148,771 | 4/1979 | Nash | 260/27 BB |
| 4,172,860 | 10/1979 | Feeney et al. | 525/97 |
| 4,288,567 | 9/1981 | Feeney et al. | 525/99 |
| 4,391,949 | 7/1983 | St. Clair | 525/99 |
| 4,444,953 | 4/1984 | St. Clair | 525/98 |
| 4,780,367 | 10/1988 | Lau et al. | 428/355 |
| 4,996,266 | 2/1991 | Bronn et al. | 525/271 |
| 5,028,646 | 7/1991 | Miller et al. | 524/77 |
| 5,057,571 | 10/1991 | Malcolm et al. | 524/505 |
| 5,075,377 | 12/1991 | Kawabuchi et al. | 525/89 |
| 5,093,430 | 3/1992 | Sakagami et al. | 525/314 |
| 5,118,762 | 6/1992 | Chin | 525/314 |
| 5,183,705 | 2/1992 | Birkholz et al. | 428/343 |
| 5,194,500 | 3/1993 | Chin et al. | 525/97 |

FOREIGN PATENT DOCUMENTS

| | | |
|---|---|---|
| 0171225A1 | 2/1986 | European Pat. Off. . |
| 0311430A2 | 4/1989 | European Pat. Off. . |
| 0451920A2 | 10/1991 | European Pat. Off. . |
| 0471998A2 | 2/1992 | European Pat. Off. . |
| 58-89672 | 5/1983 | Japan . |
| 1527226 | 10/1978 | United Kingdom . |
| 956532 | 9/1982 | U.S.S.R. . |
| WO94/01507 | 1/1994 | WIPO . |

OTHER PUBLICATIONS

Takegami et al., "New Type SIS Suitable for Double Coated Tape", Presented at the First World Congress for Pressure Sensitive Tape, Chicago, Illinois, May 6–8, 1992, pp. 71–77.

Lauck, "Label Adhesive", United States Defensive Publication No. T100,203, Jan. 06, 1981.

*Primary Examiner*—W. Robinson Clark
*Attorney, Agent, or Firm*—Pravel, Hewitt, Kimball & Krieger

[57] ABSTRACT

The invention is drawn to radial block copolymers of the formula:

$$(pS-pI-pB)_n X$$

wherein pS is polystyrene, pI is polyisoprene, pB is polybutadiene, X is the residue of a multifunctional coupling agent used in the production of the radial block copolymer, and n is a number greater than or equal to 3 representative of the number of branches appended to X; pressure sensitive adhesive compositions comprising such radial block copolymers and articles of manufacture produced therefrom. The pS component of the radial block copolymers of this invention comprise from about 14 to about 24 parts per 100 parts by weight of the radial block copolymer; the molecular weight (as polystyrene equivalent) of the radial block copolymer is between about 200,000 to about 400,000; and the weight amount of polybutadiene in the pI—pB segment is less than 50 weight percent.

28 Claims, No Drawings

RADIAL STYRENE-ISOPRENE-BUTADIENE MULTI-ARMED BLOCK COPOLYMERS AND COMPOSITIONS AND ARTICLES CONTAINING BLOCK COPOLYMERS

RELATED APPLICATION

This is a continuation-in-part of application Ser. No. 07/705,193, now U.S. Pat. No. 5,292,819, which, in turn, is a continuation-in-part application of application Ser. No. 07/393,545, now U.S. Pat. No. 5,143,968.

FIELD OF THE INVENTION

This invention relates to radial block copolymers, pressure sensitive adhesive compositions and articles constructed from such compositions. In particular, it relates to radial block copolymers comprised of polystyrene block segments and polydiene block segments. The polydiene block segment specifically is a predominately polyisoprene block containing endblock polybutadiene. The invention further relates to improved pressure sensitive adhesive compositions formed from such block copolymers and articles containing such adhesive formulations.

BACKGROUND OF THE INVENTION

This invention relates to novel block copolymers for use in pressure sensitive adhesives. More particularly, it relates to branched polystyrene-polyisoprene-polybutadiene block copolymer compositions and pressure sensitive adhesives containing such compositions.

It is known that radial block copolymers can be obtained by anionic copolymerization of a conjugated diene compound and an alkenyl arene compound by using an organic alkali metal initiator. Block copolymers have been produced which comprise primarily those having a general structure

wherein the polymer blocks A comprise thermoplastic polymer blocks of alkenyl arenes such as polystyrene, block B is a polymer block of a conjugated diene such as polyisoprene, and n is the number of branches. When the content of the alkenyl arene is small, i.e. 5–30% the produced block copolymer is a so-called thermoplastic rubber. In such a rubber, the A blocks are thermodynamically incompatible with the B blocks. Such block copolymers have been used to make pressure sensitive adhesives for a wide variety of uses including tapes, labels and product assembly applications.

Radial block copolymer commercially available under the trade name QUINTAC TM 3450 from Nippon Zeon are predominately of the (S—I)$_3$X type. The coupling efficiency of the resulting copolymer is approximately 70%. Recently, in U.S. Pat. No. 5,194,500, a three-armed (S—I)$_3$X block copolymer was described of (polystyrene equivalent molecular weight) between 180,000 and 250,000. The coupling efficiency of the copolymer was defined to be greater than 85%. The patentees stated that a direct correlation exists between increased coupling efficiency and holding power in shear.

Processing expenses as well as the need for higher cohesive strength dictate the need for more efficacious radial block copolymers. Optimum balance between high holding power and low melt viscosity has not to date been attained by the block copolymers of the prior art.

A need exists for radial block copolymers of higher holding power and shear adhesion failure temperature (SAFT) than the polymers of the prior art. An increase in these indices would permit the use of higher levels of tackifying resins and plasticizing oils in adhesive formulations from those levels presently employed. Tackifying resins and plasticizing oils are generally the least expensive components of pressure sensitive adhesive formulations.

SUMMARY OF THE INVENTION

The present invention is drawn to novel radial block copolymers comprising a polystyrene block segment and a polydiene block segment, viz. a polyisoprene block containing some polybutadiene, and improved pressure sensitive adhesive compositions which may be applied to a backing.

A further embodiment of the invention is a pressure sensitive adhesive composition which has superior shear holding power and low adhesive viscosity when applied to a backing material such as paper, foil, polymeric films, release liners of polymeric film, and woven or non-woven backing material, such as those used in packaging and fastening tapes.

DETAILED DESCRIPTION OF THE EMBODIMENTS

The invention embodies a novel radial block copolymer comprised of polystyrene block segments and polydiene block segments, suitably a predominately polyisoprene block containing a relatively small amount of polybutadiene, and a novel pressure sensitive adhesive composition comprising the copolymer, tackifying resin, stabilizer and liquid tackifying resin, plasticizing oil or combination of liquid tackifier and plasticizing oil. The pressure sensitive composition is, in particular, comprised of the radial block copolymers and a compatible tackifying resin. The polystyrene block of the radial block copolymer is of sufficiently high average molecular weight to provide, inter alia, when blended with the other components in their requisite proportions, high shear holding power and low viscosity.

The novel radial polystyrene-polyisoprene-polybutadiene block copolymer is characterized by the formula:

wherein pS is polystyrene, pI is polyisoprene, pB is polybutadiene, X is a residue of a multifunctional coupling agent used in the production of the radial block copolymer, and n is a number greater than or equal to 3 and representative of the number of branches appended to X. The number n is predominately 4. The molecular weight of the pS block of the radial block copolymer is between about 10,000 to about 15,000, preferably from about 12,000 to about 14,000. The pI—pB block preferably has a total average number molecular weight (polystyrene equivalent molecular weight) ranging from about 40,000 to about 130,000, preferably from about 50,000 to about 115,000. The overall number average molecular weight (polystyrene equivalent) of the radial block copolymer of this invention ranges from about 200,000 to about 400,000, preferably from about 225,000 to about 360,000, and the polystyrene block pS component is present in an amount of at least about 14 to about 24 parts, preferably from about 15 to about 22 parts, per 100 parts by weight of the radial block copolymer.

The radial block copolymers of this invention are thus constituted of polystyrene block segments and polydiene block in accordance with formula (1). The copolymers may be random, tapered, block or a combination of these provided that the polybutadiene segment is the terminus segment such that it may react with the coupling agent. The other endblock of the polymer is polystyrene. Each arm of the copolymer of this invention is linear.

The pS segment is generally prepared by sequentially polymerizing styrene. In accordance with formula (1), isoprene is employed to make the pI segments, the (pS—pI) polymer chains being formed by sequential polymerization of isoprene with the pS. The pS—pI—pB—Li polymer chains are then formed by the sequential polymerization of living pS—pI—Li polymer chains with butadiene.

The radial or multiblock (pS—pI—pB)$_n$X copolymers are correspondingly made by coupling the pS—pI—pB—Li living polymer chains with a multi- or tetra-functional coupling agent, such as SiCl$_4$. Thus, the styrene is polymerized to form pS, the isoprene is then introduced to form pS—pI, the butadiene is then introduced to form pS—pI—pB, and the pS—pI—pB chains are then coupled with the tetrafunctional coupling agent to form the (pS—pI—pB)$_n$X radial or multiblock polymer. The polymer will generally be recovered as a solid such as a crumb, powder or pellet.

In the pI—pB segment of the (pS—pI—pB)$_n$X polymer, the polyisoprene is present in an amount sufficient to impart predominantly polyisoprene characteristics, not butadiene or polybutadiene characteristics, to the polymer. Thus, in the pI—pB segments of the polymer, the weight amount of polyisoprene will exceed 50 percent of the total weight of diene in the polymer, i.e., pI/(pI+pB)>50 wt. %. Conversely, the weight amount of butadiene or polybutadiene will be less than 50 percent of the total weight of diene in the polymer, i.e., pB/(pI+pB)<50 wt. %. Preferably, the polybutadiene portion of the diene segment is less than 10 percent, most preferably less than 5 percent, based on the total weight of the (pI+pB), or diene component of the polymer.

The small amount of butadiene at the end of the diene midblock is useful in that it enhances the coupling reaction in formation of the polymer, and results in a radial polymer with a higher number of branches. A further description of the process at this point will facilitate an understanding of this feature of the invention. The radial polymers of this invention are thus synthesized by first contacting styrene polymer with an initiator, suitably e.g., a sec-butyllithium initiator, in the presence of an inert diluent, e.g., cyclohexane. A living polymer is then formed, as represented e.g., by the simplified structure pS—Li. The living polystyrene polymer pS—Li is next contacted with an isoprene monomer; the resulting product being represented by the simplified structure pS—pI—Li. The living polymer pS—pI—Li is then contacted with a small amount of butadiene monomer to produce a living polymer with the structure pS—pI—pB—Li, pB represents butadiene or polybutadiene. Coupling of the pS—pI—pB—Li with the coupling agent produces a branched block copolymer with the structure (pS—pI—pB)$_n$X. The radial polymer that is produced, using SiCl$_4$ as a coupling agent, will render (pS—pI—pB)$_n$X polymer where n is predominantly 4, i.e. greater than 50 weight percent of the copolymer is four arm. The butadiene need be added only in an amount necessary to assure that the ends of all of the pI segments of the polymer chains are provided with at least one molecule of butadiene, though as suggested the butadiene can be added in larger or smaller amounts. The radial block copolymers of this invention, in either event, have been found to produce unexpectedly good pressure sensitive adhesives when combined with suitable tackifier resins, plasticizer oils, and antioxidants.

Useful coupling agents are those possessing four sites reactive toward carbon-lithium bonds. Suitable coupling agents are those compositions of the formula X(L)$_n$ where X represents the coupling moiety residue, and L is suitable leaving group. Exemplary of coupling agents of this type are silicon halides, e.g., SiCl$_4$, or a silane compound where one or more of the halides is substituted by an alkoxy group, e.g. tetramethoxysilane or tetraethoxysilane compounds, epoxy compounds, e.g. epoxidized linseed oil, epoxidized soybean oil; acrylate multi esters, e.g., pentaerythritol tetraacrylate; epoxy silanes, divinyl compounds, e.g., divinyl benzene, and the like.

In addition to polystyrene, the pS component in formula (1) may be other alkenyl aromatic hydrocarbon monomers, such as alkyl-substituted styrenes, alkoxy-substituted styrenes, 2-vinyl pyridine, 4-vinyl pyridine, vinyl naphthalene, alkyl-substituted vinyl naphthalenes and the like. For simplicity herein, the terms styrene, polystyrene content-and polystyrene equivalent molecular weight are used but such terms are intended to include these other alkenyl aromatic hydrocarbons.

The isoprene polymerization technique is preferably such that the stereochemistry of the polymerizable monomer is adjusted so that predominantly cis-1,4-polyisoprene having a glass transition temperature of less than—50° C. as measured by differential scanning calorimetry at a 10° C. per minute temperature scan rate is produced.

The radial block copolymers of this invention are preferably produced by solution anionic techniques, although they could be prepared using bulk, solution or emulsion techniques. Such techniques entail contacting the monomers to be polymerized simultaneously or sequentially with an organoalkali metal compound in a suitable solvent at a temperature within the range from about—100° C. to about 150° C., preferably at a temperature within the range from about 0° C. to about 100° C. Particularly effective anionic polymerization initiators are organolithium compounds having the general formula:

$$RLi_n$$

wherein:
R is an aliphatic, cycloaliphatic, aromatic or alkyl-substituted aromatic hydrocarbon radical having from 1 to about 20 carbon atoms; and n is an integer of 1 to 3.

In general, any of the solvents known in the prior art to be useful in the preparation of such polymers may be used. Suitable solvents include straight- and branched-chain hydrocarbons such as pentane, hexane, heptane, octane and the like, as well as alkyl-substituted derivatives thereof, cycloaliphatic hydrocarbons such as cyclopentane, cyclohexane, cycloheptane and the like, as well as alkyl-substituted derivatives thereof, aromatic and alkyl-substituted aromatic hydrocarbons such as benzene, toluene, xylene and the like; hydrogenated aromatic hydrocarbons, such as tetralin, decalin and the like. Linear and cyclic ethers such as dimethyl ether, methyl ethyl ether, anisole, tetrahydrofuran and the like may be used in small amounts.

The coupling efficiency of the radial block copolymers of this invention is defined as the mass of coupled polymer divided by the mass of coupled polymer plus the mass of uncoupled polymer. The coupling efficiency herein refers to that of the original polymer not including any degradation fragments formed during processing. Thus, when producing the $(pS\text{---}pI\text{---}pB)_nX$ branched polymers of this invention, the coupling efficiency is shown by the following relationship:

$$\frac{\text{mass of coupled polymer}}{\text{mass of (uncoupled + coupled polymer)}} \times 100$$

Coupling efficiency can be measured by an analytical method such as gel permeation chromatography.

Less than maximum coupling efficiency can be achieved by a number of methods. One method to reduce coupling efficiency is to add less than the stoichiometric amount of coupling agent required for complete coupling of the polymers. Another means of reducing coupling efficiency is by the premature addition of a terminator compound. These terminators, such as water or alcohol, react very quickly and could easily be employed to cut short complete coupling of the polymers. In addition, by performing the coupling reaction at elevated temperatures, such as above about 90° C., thermal termination of many of the living polymer groups (pS—pI—Li) occurs prior to coupling. The typical coupling conditions include a temperature of between about 65° C. to about 75° C. and sufficient pressure to maintain the reactants in a liquid phase.

Following the coupling reaction or when the desired coupling efficiency has been obtained, any remaining uncoupled product is terminated such as by the addition of terminators, e.g. water, alcohol or other reagents, for the purpose of removing the lithium radical forming the nucleus for the condensed polymer product. The product is then recovered such as by coagulation utilizing hot water or steam or both, or alternatively by the use of a devolatilizing extruder.

It is preferred that the coupling efficiency of the radial block copolymer of this invention is greater than or equal to 60%. Most preferably, the coupling efficiency is between 70 to 95%.

When a polymer is made by the coupling process, the coupling efficiency of the polymer is the percentage of pS—pI—pB arms which are load bearing.

Hot melt coatable pressure sensitive adhesive compositions, constituted of a $(pS\text{---}pI\text{---}pB)_nX$ radial block copolymer to which the primary tackifying resin, the liquid tackifying resin and/or plasticizing oil and stabilizer, once heated to a temperature where it will flow readily, may be used in a wide variety of pressure sensitive applications. A particularly preferred application is their use in packaging tapes. Other uses include a wide variety of tapes, labels and assembly adhesives. Another important advantage of the compositions of the present invention is that they give much better shear holding power than similarly made polymers which also meet the industry standards. This is shown in the examples.

In particular, the adhesive of this invention may be applied from a conventional solvent or as a hot melt to a backing, preferably a flexible backing, by any of the techniques known in the art, including flow coating, roller coating, knife coating, melt blowing or spray or the like. The pressure sensitive adhesive composition may be applied to any conventional backing member such as paper, foil, polymeric film, release liners made of polymeric film or paper, woven or non-woven backing material, such as that used for packaging and fastening tapes. The pressure sensitive adhesive composition can also be extruded into place by using a hot extruder or die face. The application of the pressure sensitive adhesive composition by conventional hot melt extrusion equipment is easily facilitated because of the relatively low melt viscosity of the high shear strength of the adhesive.

The resulting coated backing material can then be slit, wound into rolls, converted into pads, or stacked in sheets, according to the desired end use.

The pI—pB component of the radial block copolymer has an average molecular weight (pS equivalent scale) ranging from about 40,000 to about 130,000, preferably from about 50,000 to about 115,000, the pS component is polystyrene having an average molecular weight ranging from about 10,000 to about 15,000, preferably from about 12,000 to about 14,000, the overall molecular weight of the block copolymer (polystyrene equivalent peak molecular weight measured by gel permeation chromatography) ranges from about 200,000 to about 400,000, preferably from about 225,000 to about 360,000, and wherein the pS component is present in an amount of at least about 14 parts up to about 24 parts, preferably from about 15 parts to about 22 parts, per 100 parts by weight of the radial block copolymer; from about 50 to about 200 parts, preferably from about 80 percent to about 150 parts, per 100 parts by weight of the radial block copolymer, of a compatible primary tackifying resin; from 0 to about 50 parts, preferably from about 5 to about 30 parts, per 100 parts by weight of the radial block copolymer, of a plasticizing oil or a liquid tackifying resin or both; and from about 0.1 percent to about 2 percent, preferably from about 0.5 percent to about 1.5 percent of a stabilizer, based on the weight of the adhesive composition.

Suitable primary tackifying resins include hydrocarbon resins, synthetic polyterpenes, rosin esters and natural terpenes which are semi-solid or solid at ambient temperatures, and soften or become liquid at temperatures ranging generally from about 70° C. to about 135° C., preferably from about 85°C. to about 120° C. Exemplary of the (solid) compatible tackifying resins at room temperature are (1) natural and modified rosins such as, for example, gum rosin, wood rosin, tall oil rosin, distilled rosin, hydrogenated rosin, dimerized rosin, and polymerized rosin; (2) glycerol and pentaerythritol esters of natural and modified rosins, such as, for example, the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natured terpenes, e.g., styrene/terpene and alpha methyl styrene/terpene; (4) polyterpene resins having a softening point, as determined by ASTM method E28-58T, of from about 80° to 150° C.; the latter polyterpene resins generally resulting from the polymerization of terpene hydrocarbons, such as the bicyclic monoterpene known as pinene, in the presence of Friedel-Crafts catalysts at moderately low temperatures; also included are the hydrogenated polyterpene resins; (5) phenolic modified terpene resins and hydrogenated derivatives thereof such as, for example, the resin product resulting from the condensation, in an acidic medium, of a bicyclic terpene and a phenol; (6) aliphatic petroleum hydrocarbon resins having a Ball and Ring softening point of from about 70° to 135° C.; the latter resins resulting from the polymerization of monomers consisting primarily of olefins and diolefins; also included are the hydrogenated aliphatic petroleum hydrocarbon resins; (7) aromatic petroleum hydrocarbon resins, and mixed aromatic and aliphatic hydrocarbon resins, and the hydrogenated derivatives thereof; (8) aromatic modified alicyclic petroleum hydrocarbon resins and the hydrogenated derivatives thereof; and (9) alicyclic petroleum hydrocarbon resins and the hydrogenated derivatives thereof. The preferred tackifying resins for use in the practice of this invention are represented by sub-paragraphs (4), (6) and (9), supra.

The adhesive composition of the instant invention may contain plasticizers, such as rubber extending plasticizers, or compounding oils or liquid resins, such as liquid tackifiers. Preferably, the adhesive formulations of this invention contain a plasticizing oil, liquid tackifier or a combination of plasticizing oil and liquid tackifying resin. Such components serve to reduce viscosity and improve tack properties.

Rubber compounding oils are well-known in the art and include both high saturates content oils and high aromatic content oils. Preferred plasticizers are highly saturated oils, e.g. TUFFLO ® 6056 oil made by Arco Chemical Company, and oils with relatively low aromatic content, e.g. SHELLFLEX ® 371 oil made by Shell Oil Company. Other plasticizing oils which have been found useful include olefin oligomers and low molecular weight polymers as well as vegetable and animal oil and their derivatives. The petroleum derived oils which may be employed are relatively high boiling materials containing only a minor proportion of aromatic hydrocarbons (preferably less than 30% and, more particularly, less than 15% by weight of the oil). Alternatively, the oil may be totally non-aromatic. The oligomers may be polypropylenes, polybutenes, hydrogenated polyisoprene, hydrogenated polybutadiene, polypiperylene and copolymers of piperylene and isoprene, or the like having average molecular weights between about 350 and about 10,000. Vegetable and animal oils include glyceryl esters of the usual fatty acids and polymerization products thereof.

Liquid tackifying resins are those tackifiers which are liquid at room temperature. Generally, the glass transition temperature of such resins is between −20° to −40° C. The softening point of such resins is generally below room temperature, i.e. between 10° to 30° C. Suitable for use are the liquefied forms of any of the (solid) tackifiers referenced above. Such liquid tackifiers generally have a lower molecular weight than their solid counterparts.

Optional components of the present invention are stabilizers which inhibit or retard heat degradation, oxidation, skin formation and color formation. Stabilizers are typically added to the commercially available compounds in order to protect the polymers against heat degradation and oxidation during the preparation, use and storage of the adhesive composition.

Additional stabilizers known in the art may also be incorporated into the adhesive composition. These may be for protection during the useful life of the product against, for example, oxygen, ozone and ultra-violet radiation. However, these additional stabilizers should be compatible with the essential stabilizers mentioned hereinabove and their intended function as taught herein.

The stabilizer, or antioxidant, used in accordance with the practice of this invention includes high molecular weight hindered phenols and multifunctional phenols such as sulfur and phosphorous-containing phenols. Hindered phenols are well known to those skilled in the art and may be characterized as phenolic compounds which also contain sterically bulky radicals in close proximity to the phenolic hyroxyl group thereof. In particular, tertiary butyl groups generally are substituted onto the benzene ring in at least one of the ortho positions relative to the phenolic hyroxyl group. The presence of these sterically bulky substituted radicals in the vicinity of the hydroxyl group serves to retard its stretching frequency and, correspondingly, its reactivity; this steric hinderance thus providing the phenolic compound with its stabilizing properties. Representative hindered phenols include 1,3,5-trimethyl 2,4,6-tris (3,5-di-tert-butyl-4-hydroxybenzyl) benzene; pentaerythrityl tetrakis-3 (3,5-di-tertbutyl-4-hydroxyphenyl) propionate; n-octadecyl-3; 3,5-di-tert-butyl-4-hydroxyphenyl)-propionate; 4,4'-methylenbis (2,6-tert-butylphenol); 4,4'-thiobis (6-tert-butyl-o-cresol); 2,6-di-tert-butylphenol; 6-(4-hydroxyphenoxy)-2,4-bis(n-octyl-thio)-1,3,5 21 triazine; di-n-octadecyl 3,5-di-tert-butyl-4-hydroxy-benzylphosphonate; 2-(n-octylthio) ethyl 3,5-di-tert-butyl-4-hydroxy-benzoate; and sorbitol [hex 3-(3,5-di-tert-butyl-4-hydroxyphenyl)-propionate.]

The adhesive composition is prepared for use by blending the radial block copolymer with the primary tackifying resin, the liquid tackifying resin or plasticizing oil, and stabilizer, in any order or sequence, or those materials can be added together simultaneously to form the adhesive composition. The components may be mixed, if desired, either in solution as dry granules or melt blending. In commercial practice it would be expected that the primary tackifying resin and copolymer with optional stabilizer, with or without the simultaneous addition of the liquid tackifying resin or plasticizing oil, would be blended together at sufficiently elevated temperature to form a fluid melt. For example, the copolymer can be blended with the solid compatible primary tackifying resin at temperatures ranging from about 130° C. to about 220° C., preferably at from about 150° C. to about 220° C., to form a fluid melt. The secondary liquid tackifying resin, or plasticizing oil, and stabilizer, can then be added to the melt. Alternatively, the fluid melt can be prepared with all components of the adhesive composition present ab initio.

The adhesive compositions of the present invention are often prepared by blending the components at an elevated temperature, preferably between about 130° C. and about 200° C., until a homogeneous blend is obtained, usually less than three (3) hours. Various methods of blending are known to the art and any method that produces a homogeneous blend without undue degradation is satisfactory. Still, the copolymer and the extending oil, if desired, can be blended together readily at moderately elevated temperatures, e.g., 200 to 350° F. (95° to 180° C.). The tackifying resin can be added to the copolymer/oil blend. Further, the extending oil and tackifying resin can be admixed and then added to the copolymer. If a pigment is included in the pressure sensitive adhesive composition, it should be added to the copolymer/oil blend before or at the same time that the tackifying resin is introduced into the composition to achieve optimum dispersion.

Various other components can be added to modify the tack, rheology characteristics (including melt viscosity, thixotropy), adhesive bond strength characteristics, rate of "set", low temperature flexibility, color, odor, etc. of a hot-melt pressure sensitive adhesive composition. For example, liquid or low-melting resins, i.e., resins having ring and ball softening points up to 40° C., can sometimes be used as a partial or total replacement or substitution for extending oils.

The following non-limiting examples, and comparative demonstrations, bring out the more salient features of this invention. All parts are given in terms of weight units except as may otherwise be indicated.

EXAMPLES

In conducting the following tests the composition and properties of the block copolymers which were prepared for making the adhesive compositions were determined by techniques "a" and "b". In evaluating the performance characteristics of the adhesive compositions produced from the block copolymers test procedures "c" through "e" were employed.

a. Styrene Content—of the experimental copolymers was determined from the refractive index of an optically homogeneous pressed polymer film (less than 0.02 inch in thickness) in accordance with ASTM D 542-50. The Refractive Index Value was converted to weight percent styrene using a statistical correlation derived from a set of gravimetrically prepared standards. See further R. H. Wiley and P. H. Hobson, "Determination of Refractive Index of Polymers", *Analytical Chemistry XX*, June, 1984, pp. 520–523.

b. Molecular Weight—and coupling efficiency, percent 3-arm and percent 4-arm of the block copolymers was determined by gel permeation chromatography (GPC).

c. Adhesive Melt Viscosity (ASTM D-3236)—melt viscosities were measured at a temperature of 177° C., using a Brookfield Thermosel viscometer.

d. Shear Adhesion Failure Temperature (SAFT)—is a measure of the ability of the bond to withstand an elevated temperature rising at 10° F./15 min., under a constant force which pulls the bond in the shear mode. Bonds 1 inch by 1 inch were formed of adhesive, on a Mylar (polyester) backing, to a stainless steel panel, using a 4.5 lb. rubber roller. The panel was suspended vertically in an oven at 32° C., and allowed to come to equilibrium. A 1 kg weight was suspended from the free end of the adhesive tape, and the temperature was raised at 10° F./15 min. The temperature at which the tape and weight fell from the panel was recorded. SAFT was reported as the average of three such determinations.

e. Shear Holding Power (Static Time to Failure Bond Test)—the cohesive strength of the adhesives was determined according to the general procedures outlined in PSTC-7 and ASTM D-3654. A 1 inch by 0.5 inch bond was applied to a stainless steel panel with a 4.5 rubber roller. The plate was suspended vertically and allowed to equilibrate at 75° C. A 1 lb. weight was suspended from the free end of the tape. The time at which the tape and weight fell from the panel was recorded. The shear hold (in minutes) was reported as the average of four such determinations. Long failure times are desirable, since they indicate strong bonds.

EXAMPLE 1

To a 5 gallon stirred reactor under a nitrogen atmosphere were added 12.5 kg of cyclohexane solvent and 77.5 g of a 0.33 M solution of sec-butyl lithium in cyclohexane. The temperature of the reactor was brought to 50° C. and 425.8 g of styrene was added. Polymerization of the styrene was allowed to continue for 46 minutes. The reaction mixture was cooled to 50° C. and 1601.9 g of isoprene was added. The isoprene was allowed to polymerize for 30 minutes, during which the reaction temperature reached a maximum of 77.3° C. At the end of the 30 minutes, 20 grams of butadiene was added and it was allowed to polymerize for an additional 17 minutes. Then 49.4 g of 0.13 M $SiCl_4$ was added all at once. The reaction was allowed to continue for another 24 minutes before an excess of isopropanol was added to the polymer solution, which was then devolatilized in a vacuum oven under nitrogen at 100° C. for 3 hours.

EXAMPLE 2

To a 5 gallon stirred reactor under a nitrogen atmosphere were added 12.5 kg of cyclohexane solvent and 77.6 g of a 0.33 solution of sec-butyl lithium in cyclohexane. The temperature of the reactor was brought to 50° C. and 426.1 g of styrene was added. Polymerization of the styrene was allowed to continue for 45 minutes. The reaction mixture was cooled to 50° C. and 1603 g of isoprene was added. The isoprene was allowed to polymerize for 36 minutes, during which the reaction temperature reached a maximum of 76.1° C. At the end of the 36 minutes, 40 grams of butadiene was added and it was allowed to polymerize for an additional 37 minutes. Then 39.6 g of 0.165 M $SiCl_4$ was added all at once. The reaction was allowed to continue for another 15 minutes before an excess of isopropanol was added to the polymer solution, which was then devolatilized in a vacuum oven under nitrogen at 100° C. for 3 hours.

EXAMPLE 3

This sample was prepared by mixing together (20% solids in cyclohexane) a 50/50 blend of the reaction product from Example 1 and Example 2. The resulting solution was then devolatilized in a vacuum oven under nitrogen at 100° C. for 3 hours.

EXAMPLE 7

To a 5 gallon stirred reactor under a nitrogen atmosphere were added 12.5 kg of cyclohexane solvent and 90.5 g of a 0.289 M solution of sec-butyl lithium in cyclohexane. The temperature of the reactor was brought to 60° C. and 473.9 g of styrene was added. Polymerization of the styrene was allowed to continue for 43 minutes. The reaction mixture was cooled to 60° C. and 1560 g of isoprene was added. The isoprene was allowed to polymerize for 30 minutes, during which the reaction temperature reached a maximum of 88° C. At the end of the 30 minutes, 10 grams of butadiene was added and it was allowed to polymerize for an additional 15 minutes. Then 8.25 g of 0.4364 M $SiCl_4$ was added. The reaction was allowed to continue for another 5 minutes and then an additional 8.25 g of 0.4364 M $SiCl_4$ was added. The reaction was allowed to continue for an additional 10 minutes before an excess of isopropanol was added to the polymer solution which was then devolatilized in a vacuum oven under nitrogen at 100° C. for 3 hours.

EXAMPLE 8

To a 5 gallon stirred reactor under a nitrogen atmosphere were added 12.1 kg of cyclohexane solvent and 72 g of a 0.3356 M solution of sec-butyl lithium in cyclohexane. The temperature of the reactor was brought to 50° C. and 346.2 g of styrene was added. Polymerization of the styrene was allowed to continue for 45 minute. The reaction mixture was cooled to 50° C. and 1961.7 g of isoprene was added. The isoprene was allowed to polymerize for 35 minutes during which the reaction temperature reached a maximum of 87° C. At the end of the 35 minutes, 10 grams of butadiene was added and it was allowed to polymerize for an additional 15 minutes. Then 47.3 g of 0.141 M $SiCl_4$ was added all at once. The reaction was allowed to continue for another 15 minutes before an excess of isopropanol was added to the polymer solution, which was then devolatilized in a vacuum oven under nitrogen at 100° C. for 3 hours.

DEMONSTRATION 4

To a 5 gall stirred reactor under a nitrogen atmosphere were added 12.5 kg of cyclohexane solvent and 77.5 g of a 0.33 M solution of sec-butyl lithium in cyclohexane. The temperature of the reactor was brought to 51° C. and 425.7 g of styrene was added. Polymerization of the styrene was allowed to continue for 46 minutes. The reaction mixture was cooled to 51° C. and 1601.6 g of isoprene was added. The isoprene was allowed to polymerize for 33 minutes, during which the reaction temperature reached a maximum of 76.9° C. No butadiene was added. At the end of the 33 minutes, 46.1 g of 0.130 M $SiCl_4$ was added all at once. The reaction was allowed to continue for another 16 minutes before an excess of isopropanol was added to the polymer solution, which was then devolatilized in a vacuum oven under nitrogen at 100° C. for 3 hours.

DEMONSTRATION 5

To a 5 gallon stirred reactor under a nitrogen atmosphere were added 12.4 kg of cyclohexane solvent and 77.4 g of a 0.33 M solution of sec-butyl lithium in chlorohexane. The temperature of the reactor was brought to 50° C. and 425.4 of styrene was added. Polymerization of the styrene was allowed to continue for 46 minutes. The reaction mixture was cooled at 50° C. and 1600.2 g of isoprene was added. The isoprene was allowed to polymerize for 33 minutes during which the reaction temperature reached a maximum of 77.6° C. No butadiene was added. At the end of the 33 minutes, 59.2 g of 0.130 M $SiCl_4$ was added all at once. The reaction was allowed to continue for another 17 minutes before an excess of isopropanol was added to the polymer solution, which was then devolatilized in a vacuum oven under nitrogen at 100° C. for 3 hours.

DEMONSTRATION 6

To a 5 gallon stirred reactor under a nitrogen atmosphere were added 12.4 kg of cyclohexane solvent and 77.5 g of a 0.33 m solution of sec-butyl lithium in cyclohexane. The temperature of the reaction was brought to 50° C. and 425.6 g of styrene was added. Polymerization of the styrene was allowed to continue for 46 minutes. The reaction mixture was cooled to 50° C. and 1601 g of isoprene was added. The isoprene was allowed to polymerize for 33 minutes, during which the reaction temperature reached a maximum of 77.8° C. No butadiene was added. At the end of 33 minutes, 51.8 g of 0.165 M trisnonylphenylphosphite (TNPP) was added all at once. The reaction was allowed to continue for another 17 minutes before an excess of isopropanol was added to the polymer solution, which as then devolatilized in a vacuum oven under nitrogen at 100° C. for 3 hours.

DEMONSTRATION 9

To a 5 gallon stirred reactor under a nitrogen atmosphere were added 12.5 kg of cyclohexane solvent and 90.5 g of a 0.289 M solution of sec-butyl lithium in cyclohexane. The temperature of the reactor was brought to 60° C. and 473.9 g of styrene was added. Polymerization of the styrene was allowed to continue for 43 minutes. The reaction mixture was cooled to 60° C. and 1560 g of isoprene was added. The isoprene was allowed to polymerize for 30 minutes during which the reaction temperature reached a maximum of 88° C. No butadiene was added. At the end of the 30 minutes, 16.5 g of 0.4364 M $SiCl_4$ was added. The reaction was allowed to continue for an additional 15 minutes before an excess of isopropanol was added to the polymer solution, which was then devolatilized in a vacuum oven under nitrogen at 100° C. for 3 hours.

DEMONSTRATION 10

To a 5 gallon stirred reactor under a nitrogen atmosphere were added 12.1 kg of cyclohexane solvent and 72.2 g of a 0.3356 M solution of sec-butyl lithium in cyclohexane. The temperature of the reactor was brought to 50° C. and 346.2 g of styrene was added. Polymerization of the styrene was allowed to continue for 45 minutes. The reaction mixture was cooled to 5020 C. and 1961.7 g of isoprene was added. The isoprene was allowed to polymerize for 35 minutes during which the reaction temperature reached a maximum of 90° C. No butadiene was added. At the end of the 35 minutes, 47.3 g of 0.141 M $SiCl_4$ was added all at once. The reaction was allowed to continue for another 15 minutes before an excess of isopropanol was added to the polymer solution, which was then devolatilized in a vacuum oven under nitrogen at 100° C. for 3 hours.

FORMULATION EXAMPLES

Adhesive compositions were prepared by blending the block copolymer, a primary tackifying resin, ESCOREZ ® 2596 (a product of Exxon Chemical Co.), a plasticizer oil, TUFFLO ® 6056 (a product of Lyondell Petroleum Co.), and a stabilizer, IRGANOX ® 1010, a product of Ciba-Geigy), to produce a homogeneous adhesive blend, according to the amounts outlined in the table below.

|  | Formulation 1 | Formulation 2 |
| --- | --- | --- |
| Block Copolymer | 100 | 100 |
| Tackifier | 125 | 150 |
| Oil | 15 | 20 |
| Stabilizer | 1 | 1 |

The adhesive was coated onto 2 mil thick Mylar (polyester) backing, to produce a 1.5 mil thick film of adhesive.

The performance characteristics of the resulting adhesives are given in the Table below. The adhesive formulation for the (pS—pI-pB)$_x$—X radial block copolymers or "rubbers" of this invention are designated as Examples 1, 2, 3, 7 and 8.

Demonstrations 4, 5, 6, 9 and 10 are $(SI)_3X$ block copolymers and are provided for comparative purposes. QUINTAC® 3450 is a commercially available predominatly 3-arm $(SI)_3X$ copolymer of Nippon Zeon and has been promoted for use in pressure sensitive packaging tapes. See "New Type SIS Suitable for Double-Coated Tape", Hiroshi Takegami, Proceedings of the PSTC Conference, 1992. VECTOR® 4111 and VECTOR® 4113, products of Dexco Polymers, are linear SIS block copolymers and are widely used in pressure sensitive adhesives for tapes and labels.

Demonstration 5 illustrates the adhesive performance of a 3-armed $(SI)_n-X$ polymer as discussed in U.S. Pat. No. 5,194,500. Example 1 is a predominatly 4-arm $(SIB)_xX$ polymer in which the molecular weight of each of the 4 (SIB) arms is almost identical to the molecular weight of each of the 3 arms of (SI) in Demonstration 5. Example 1 has approximately the same coupling efficiency (load-bearing capacity), and styrene content as Demonstration 5. The addition of 1.2% pB (based on weight of pI+pB) in Example 1, produces a polymer with predominantly 4 arms as opposed to predominantly 3 arms in Demonstration 5. The unexpected benefits in adhesive performance can be seen in the higher shear holding power and heat resistance (SAFT) of Example 1 compared to Demonstration 5.

The higher shear holding power and SAFT of the $(SIB)_nX$ polymers of this invention allows them to be formulated with higher levels of tackifier resin and plasticizer oil. This is illustrated by examining the adhesive performance in Formulation 2, which contains only 37 weight percent block copolymer, compared to 41 weight percent block copolymer in Formulation 1. The block copolymer is the most expensive component of the formulation. As a result, Formulation 2 has a lower raw material cost than Formulation 1. Examples 1 and 3 of this invention exhibit unexpectedly good adhesive performance in Formulation 2 when compared to the 3-arm $(SI)_3X$ polymers (Demonstration 5, Demonstration 6, QUINTAC 3450) as well as the widely used linear products VECTOR® 4111 and VECTOR® 4113. In fact the $(SIB)_nX$ polymers of this invention exhibit better shear-holding power and SAFT in the low-rubber Formulation 2, than all of the commercially available polymers (VECTOR® 4111, VECTOR® 4113, QUINTAC 3450) exhibit in the high-rubber Formulation 1. In addition, the Formulation 2 adhesives have lower adhesive viscosity than Formulation 1, which allows for easier processing.

The impact of coupling efficiency on adhesive performance can be seen by comparing the adhesive performance of Examples 1, 2 and 3. These predominantly 4-arm $(SIB)_nX$ polymers are essentially identical, with the exception of percent coupling efficiency. As the percent coupling efficiency decreases, the shear holding power and SAFT also decrease. However, as shown in Example 2, even at a coupling efficiency as low as 71% the shear holding power and SAFT of the $(SIB)_nX$ polymers is significantly better than that exhibited by the two commercially available linear SIS polymers, VECTOR® 4111 and VECTOR® 4113, as well as the predominantly 3-arm $(SI)_nX$ polymer commercially available as QUINTAC 3450. Note that QUINTAC 3450 also has a coupling efficiency, styrene content, and arm molecular weight nearly identical to that of Example 2.

Examples 7 and 8 are provided to illustrate the performance of $(SIB)_nX$ polymers at the upper and lower ends of the percent styrene range described in this invention. Notice that in each case the performance is superior to that of a 3-arm $(SI)_3X$ polymer at equal styrene content and arm molecular weight. In addition, note that the shear holding power and SAFT of both Example 7 and Example 8 is superior to that displayed by the linear SIS polymers, VECTOR® 4111 and VECTOR® 4113, both of which are widely used commercially in pressure sensitive tape and label adhesives.

| Sample | Type | % styr | % PB in PI + PB | Arm Mol Wt | Main Pk Mol Wt | % 3-arm | % 4-arm |
| --- | --- | --- | --- | --- | --- | --- | --- |
| Example 1 | $(SIB)_n-X$ | 21.2 | 1.2 | 85492 | 282998 | 22 | 70 |
| Demonstration 5 | $(SI)_3-X$ | 21.2 | 0 | 83273 | 222442 | 89 | 0 |
| Example 3 | $(SIB)_n-X$ | 21 | 1.8 | 85039 | 287887 | 24 | 58 |
| Demonstration 6 | $(SI)_3-Y$ | 21.9 | 0 | 81923 | 214813 | 80 | 0 |
| Example 2 | $(SIB)_n-X$ | 20.7 | 2.4 | 84140 | 281392 | 14 | 57 |
| QUNTAC 3450 | $(SI)_n-X$ | 20 | 0 | 83247 | 223064 | 40 | 29 |
| Demonstration 4 | $(SI)_3-X$ | 21 | 0 | 86934 | 229780 | 72 | 0 |
| Example 7 | $(SIB)_n-X$ | 23.7 | 0.51 | 85339 | 266258 | 20 | 55 |
| Demonstration 9 | $(SI)_3-X$ | 23.7 | 0 | 86038 | 229722 | 75 | 0 |
| Example 8 | $(SIB)_n-X$ | 16 | 0.51 | 102288 | 316071 | 22 | 65 |
| Demonstration 10 | $(SI)_3-X$ | 16 | 0 | 105128 | 288051 | 77 | 0 |
| VECTOR® 4111 | SIS | 18 | | | 171500 | 0 | 0 |
| VECTOR® 4113 | SIS | 15 | | | 201500 | 0 | 0 |

| Sample | Coupling Effic. | SAFT(C) Form 1 | SAFT(C) Form 2 | 75C SHEAR Form 1 | 75C SHEAR Form 2 | VISC Form 1 | VISC Form 2 |
| --- | --- | --- | --- | --- | --- | --- | --- |
| Example 1 | 92 | 107.1 | 99.7 | >7000 | 4542 | 162200 | 61500 |
| Demonstration 5 | 89 | 104.6 | 97.3 | 3264 | 1045 | 58300 | 36000 |
| Example 3 | 82 | 101.4 | 96.4 | 3018 | 1224 | 62800 | 31450 |
| Demonstration 6 | 80 | 99.9 | 94.8 | 1657 | 715 | 56200 | 28500 |
| Example 2 | 71 | 98.6 | 98.6 | 1617 | 717 | 41000 | 25050 |
| QUNTAC 3450 | 69 | 94.2 | | 384 | | 33000 | |
| Demonstration 4 | 72 | 99.2 | 94.3 | 1146 | 797 | 64500 | 37500 |
| Example 7 | 75 | 105 | | 4200 | | 225000 | |
| Demonstration 9 | 75 | 102 | | 3000 | | 168400 | |
| Example 8 | 87 | 98 | | 1171 | | 67600 | |
| Demonstration 10 | 77 | 97 | | 724 | | 42400 | |
| VECTOR® 4111 | 100 | 96.5 | 91.4 | 438 | 86 | 67400 | 31600 |

-continued

| VECTOR ® 4113 | 82 | 93 | 88.7 | 205 | 66 | 53300 | 30700 |

What is claimed is:

1. A radial block copolymer comprising (i) a polystyrene block segment and (ii) a polyisoprene block segment having an end which comprises butadiene, wherein the block copolymer is characterized by the formula:

$$(pS\text{---}pI\text{---}pB)_n X$$

pS being polystyrene, pI being polyisoprene, pB being polybutadiene, X being the residue of a multifunctional coupling agent used in the production of the radial block copolymer and n being a number greater than or equal to 3 and representing the number of branches appended to X, and further wherein
   the pS component is present in an amount of at least 14 parts to about 24 parts per 100 parts by weight of the radial block copolymer; and
   the weight amount of polybutadiene in the pI—pB segment being less than 50 weight percent.

2. The radial block copolymer of claim 1 wherein the weight amount of polybutadiene in the pI—pB segment is less than 10 weight percent and the overall number average molecular weight of the radial block copolymer is between about 200,000 to about 400,000.

3. The radial block copolymer of claim 2 wherein the pS component is between about 15 to about 22 parts per 100 parts by weight of the copolymer.

4. The radial block copolymer of claim 2 wherein the coupling efficiency of the block copolymer is greater than or equal to 60%.

5. The radial block copolymer of claim 4 wherein the coupling efficiency of the block copolymer is between about 70% to about 95%.

6. The radial block copolymer of claim 2 wherein the average number molecular weight of the pS component is between about 10,000 to about 15,000.

7. The radial block copolymer of claim 6 wherein the average number molecular weight of the pS component is between about 12,000 to about 14,000.

8. The radial block copolymer of claim 2 where n is predominately 4.

9. The radial block copolymer of claim 2 wherein the weight amount of polybutadiene in the pI—pB segment is less than or equal to 5 percent.

10. The radial block copolymer of claim 1 wherein the overall number average molecular weight of the radial block copolymer is between about 225,000 to about 360,000.

11. A pressure sensitive adhesive composition comprising a primary tackifying resin and the radial block copolymer of claim 1.

12. The pressure sensitive adhesive composition of claim 11 wherein the tackifying resin is present in an amount of from about 50 parts to about 200 parts by weight per hundred parts by weight of the copolymer.

13. The pressure sensitive adhesive composition of claim 12 wherein the tackifying resin is present in an amount of from about 80 parts to about 150 parts by weight per hundred parts by weight of the block copolymer.

14. The pressure sensitive adhesive composition of claim 11 wherein
   (i) the pS component is between 15 to about 22 parts per 100 parts by weight of the block copolymer;
   (ii) n is predominately 4; and
   (iii) the coupling efficiency of the block copolymer is greater than or equal to 60%.

15. The pressure sensitive adhesive composition of claim 14 wherein the coupling efficiency of the block copolymer is between about 70 to about 95%.

16. The pressure sensitive adhesive composition of claim 14 further comprising up to 50 parts per hundred parts of block copolymer of extender oil by weight.

17. The pressure sensitive adhesive composition of claim 14 wherein the composition is either hot melt coatable or solvent-coatable.

18. An article comprising a substrate having on at least one major surface thereof a layer of the composition of claim 12.

19. A tape comprising a backing layer having on at least one major surface thereof a layer of the composition of claim 12.

20. The tape of claim 19 wherein the backing is made of paper.

21. The tape of claim 19 wherein the backing is made of a polymeric material.

22. The pressure sensitive adhesive composition of claim 16 wherein the composition is either hot melt coatable or solvent-coatable.

23. An article comprising a substrate having on at least one surface thereof a layer of the composition of claim 16.

24. A tape comprising a backing layer having on at least one major surface thereof a layer of the composition of claim 16.

25. The tape of claim 24 wherein the backing is made of paper.

26. The tape of claim 24 wherein the backing is made of a polymeric material.

27. The pressure sensitive adhesive composition of claim 11 wherein the primary tackifying resin is solid at room temperature.

28. The pressure sensitive adhesive composition of claim 27 further comprising a second tackifying resin which is liquid at room temperature.

* * * * *